US006953056B1

(12) United States Patent
Chrisp

(10) Patent No.: US 6,953,056 B1
(45) Date of Patent: Oct. 11, 2005

(54) METERING VALVE ASSEMBLY

(76) Inventor: Lynn E. Chrisp, 17240 W. Hwy. 6, Kenesaw, NE (US) 68956

( * ) Notice: Subject to any disclaimer, the term of this patent is extended or adjusted under 35 U.S.C. 154(b) by 195 days.

(21) Appl. No.: 10/375,186

(22) Filed: Feb. 26, 2003

(51) Int. Cl.$^7$ ................................................. F16K 1/04
(52) U.S. Cl. .................... 137/625.33; 251/267
(58) Field of Search ........................ 137/625.3, 625.33; 251/266, 267, 268, 269

(56) References Cited

U.S. PATENT DOCUMENTS

| | | |
|---|---|---|
| 1,619,937 A | 3/1927 | Huff |
| 2,784,933 A | 3/1957 | Newell et al. ............... 251/225 |
| 2,980,392 A | 4/1961 | Greenwood .................. 251/210 |
| 3,086,749 A | 4/1963 | Frye ............................ 251/205 |
| 3,139,262 A | 6/1964 | Morris et al. ............... 251/205 |
| 3,365,166 A | 1/1968 | Smith .......................... 251/121 |
| 3,410,521 A | 11/1968 | Sowers, III et al. ......... 251/205 |
| 3,511,470 A | 5/1970 | Beckett et al. .............. 251/121 |
| 3,521,852 A | 7/1970 | Gillis, Jr. ..................... 251/121 |
| 3,794,249 A | 2/1974 | Lockwood ................... 239/539 |
| 3,985,331 A | 10/1976 | Riley et al. .................... 251/77 |
| 4,157,808 A | 6/1979 | Eidsmore .................... 251/205 |
| 4,230,300 A * | 10/1980 | Wiltse ......................... 251/205 |
| 6,299,134 B1 | 10/2001 | Laaja .......................... 251/205 |

* cited by examiner

Primary Examiner—John Fox
(74) Attorney, Agent, or Firm—Thomte, Mazour & Niebergall; Shane M. Niebergall

(57) ABSTRACT

A metering valve assembly is provided with a valve stem having one or more tapered channels formed therein for selective engagement with a valve seat to provide incremental regulation of fluid flow through a valve housing. An adjustment knob provides one manner of reciprocal movement of the valve stem within the valve housing. Alternatively, the valve stem can be directly engaged for rotational reciprocal movement within the valve housing. Different embodiments of the valve stem are provided for alternate fluid flow regulation requirements. The metering valve assembly is comprised of a limited number of component parts for ease of manufacture as well as the replacement and exchange of component parts in the field.

18 Claims, 3 Drawing Sheets

US 6,953,056 B1

METERING VALVE ASSEMBLY

BACKGROUND OF THE INVENTION

The present invention relates to valve assemblies and more particularly to micro-metering valves used to regulate the micro flow rates of various fluids.

DESCRIPTION OF THE PRIOR ART

Micro-metering valves are widely used in various industries to regulate the micro flow rates of fluids ranging from liquid agricultural seed treating chemicals to medical and biochemical gas applications. Two of the more common types of micro-metering valves used are needle valves, which are comprised of elongated tapered valve stems and a valve seat; and ball valves, which are comprised of a rotatable sphere having a fluid passageway formed therethrough. Either of these valves can be constructed in an in-line or tee fashion, depending on the needs of the particular application. However, prior art micro-metering valves typically suffer from one or more of a handful of shortcomings.

More often than not, "micro-metering" valves provide a limited range of variable flow control. Tapered needle valves typically require a substantially elongated and tapered tip to provide a wide range of accurate flow variance. Such valves are often difficult to manufacture for a wide range of incremental flow regulation and are comprised of delicate operating components. Ball valves are typically comprised of a uniform diameter opening for the passage of fluids. Accordingly, the range of fluid flow variance is dependent upon the system's ability to make accurate and minute movements of the ball opening with respect to a valve seat. The cost and complexity of the manufacturing process for such valves can rise dramatically as the degree of accuracy increases.

Prior art valve systems provide limited options for the user who must repair or interchange a component part of the valve system. Most micro-metering valves are manufactured as a "closed system" that must be wholly discarded and replaced in such situations. Those valve systems which are open systems capable of refurbishment are comprised of component mechanisms whose manufacturing tolerances may be insufficient to allow for accurate and convenient component part replacement.

The prior art also fails to provide valve assemblies with alternate means for the movement of the valve's component parts. Most valve assemblies are provided only with a thumb-screw or handle for actuation of the valve. Accordingly, the user is often left without an alternate means for valve actuation when the primary means becomes fouled due to environmental conditions, foreign debris, or mechanical failure. Moreover, valve assemblies having a single actuation means typically lack the capability of further micro-adjustment once the primary actuation means has positioned the valve's component parts.

Accordingly, what is needed is a new micro-metering valve assembly that provides a wide range of variable fluid flow regulation that is also simple in manufacture and use.

SUMMARY OF THE INVENTION

The metering valve of the present invention is generally provided with an elongated valve stem having one or more generally tapered grooves formed at one end of the valve stem and mating threads formed in the opposite end. The valve stem is at least partially disposed within a valve housing having an inlet portion, an outlet portion, and an adjustment portion. The adjustment portion is generally provided with an adjustment knob that threadably engages the valve stem at one end. An adjustment coupling is secured at one end to the adjustment portion of the valve housing and is rotatably secured at its opposite end to the adjustment knob. In this arrangement, rotation of the adjustment knob provides for reciprocal, non-rotational movement of the valve stem within the valve housing. Optionally, the adjustment end of the valve stem can be shaped to receive a rotating means to initiate rotational reciprocal movement of the valve stem with respect to the valve housing and the adjustment knob.

The valve stem is selectively coaxially received by a valve seat disposed within the output portion of the valve housing. Reciprocal movement of the valve stem within the valve housing positions the tapered channel in the valve stem with respect to an opening in the valve seat. Accordingly, fluid flow through the valve assembly can be incrementally regulated. Full advancement of the valve stem within the housing engages a generally tapered shoulder portion of the valve stem with the valve seat to provide a positive stop for the fluid flow. A hip member formed in the valve stem adjacent to the shoulder member is sized to prevent the complete withdrawal of the valve stem through the adjustment coupling member. Alternate valve stems having different flow regulation features can be selectively exchanged to adapt the function of the valve assembly's flow regulation.

The metering valve is assembled with a limited number of component parts to simplify the manufacturing process. Each of the component parts are assembled and disassembled easily for replacement or exchange of component parts in the field as circumstances dictate.

It is therefore a principal object of the present invention to provide a metering valve that is capable of a wide range of fluid flow adjustment.

A further object of the present invention is to provide a metering valve that is simple in manufacture and use.

Yet another object of the present invention is to provide a metering valve that provides for easy disassembly and interchangement of component parts.

Still another object of the present invention is to provide a metering valve that provides for multiple methods of valve stem advancement and retraction.

A further object of the present invention is to provide a metering valve capable of regulating the flow of a wide range of liquids and gases.

These and other objects will be apparent to those skilled in the art.

DESCRIPTION OF THE PREFERRED EMBODIMENT

Figure 1:
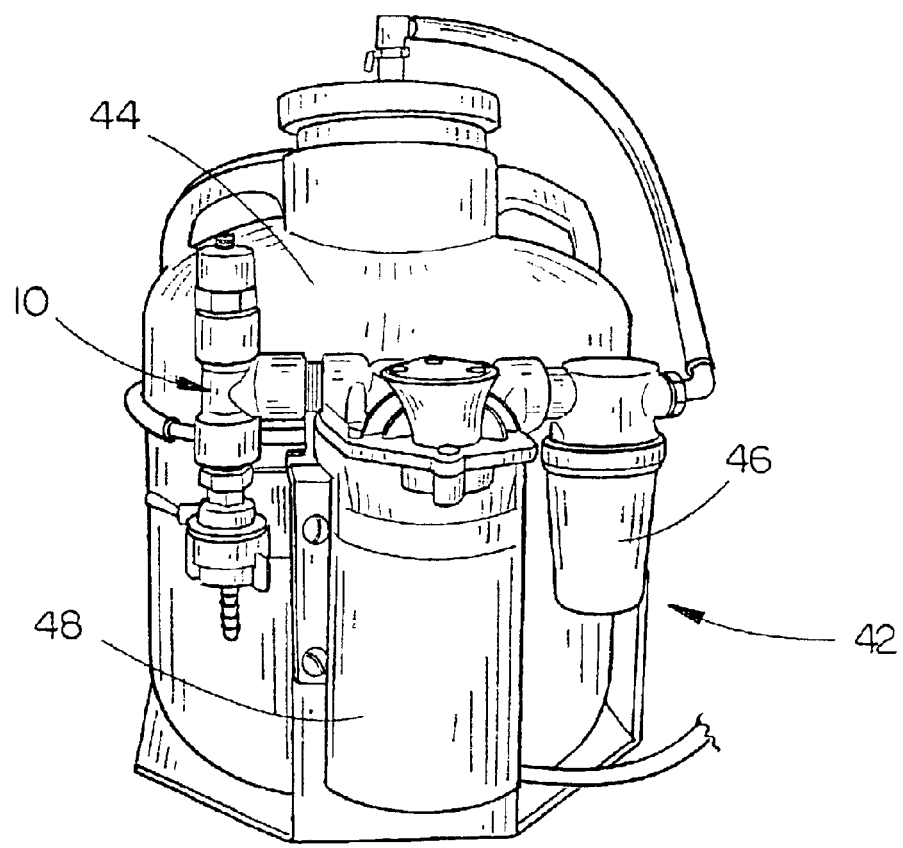
FIG. 1 depicts one possible application for the metering valve of the present invention.

The numeral 10 refers generally to the metering valve assembly of this invention as depicted in FIGS. 1–6. The valve assembly 10 is provided with an elongated valve stem 12 having an adjustment end 14 and a regulating end 16. The regulating end 16 of the valve stem 12 is shaped to be releasably and slidably received within the opening of a valve seat 18. In a preferred embodiment, the adjustment end 14 of the valve stem 12 is slidably received through an adjustment coupling member 20. The adjustment end 14 is then threadably received by an adjustment knob 22. The adjustment knob 22 is provided with an open inner portion for at least partially receiving the upper end of the adjustment coupling member 20 therein. A first generally annular channel 24 is formed within the open inner chamber of the adjustment knob 22. A second generally annular channel 26 is formed within the periphery of the upper end of the adjustment coupling member 20 so that the first and second channels 24 and 26 are positioned closely adjacent one another when the adjustment knob 22 and the adjustment coupling member 20 are mated together. The first and second channels 24 and 26 are sized to receive a generally annular retention ring 28. The retention ring 28 helps secure the adjustment knob 22 and the adjustment coupling member 22 in rotatable connection with one another.

Figure 2:
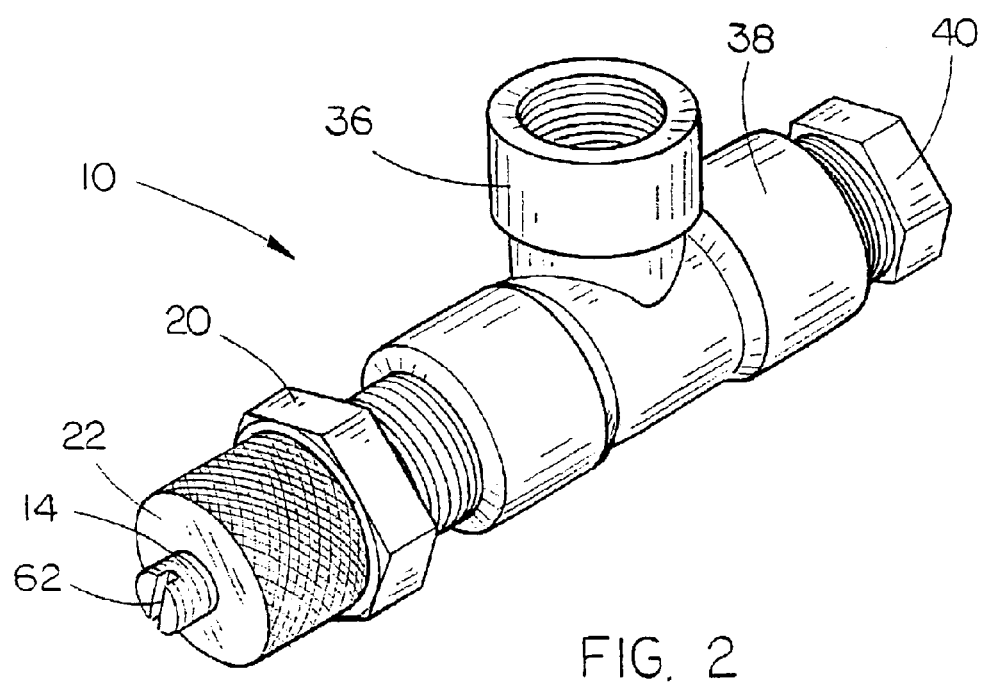
FIG. 2 is a perspective view of the metering valve of the present invention in an assembled form.
Figure 3:
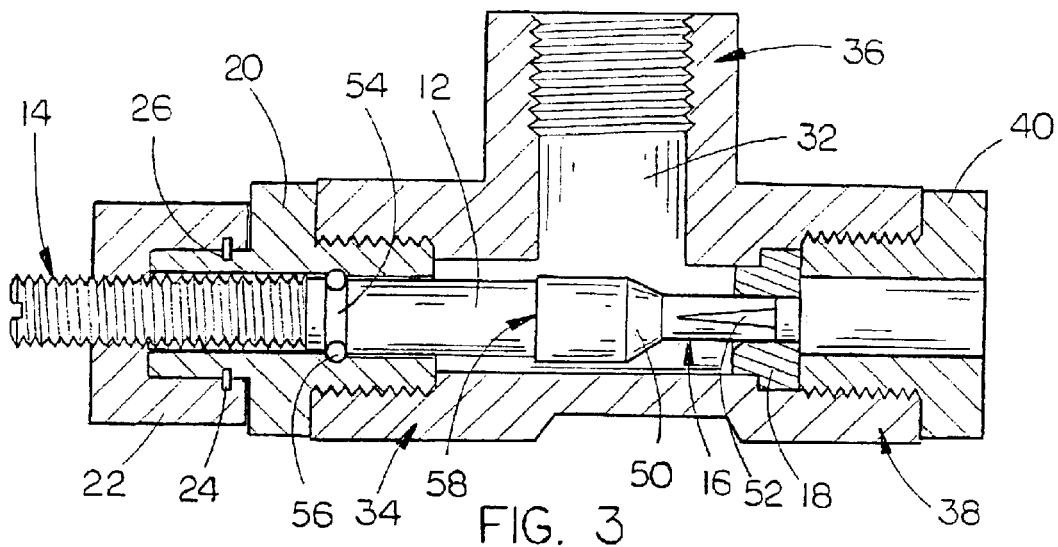
FIG. 3 is a side cutaway view of the metering valve of the present invention.
Figure 4:
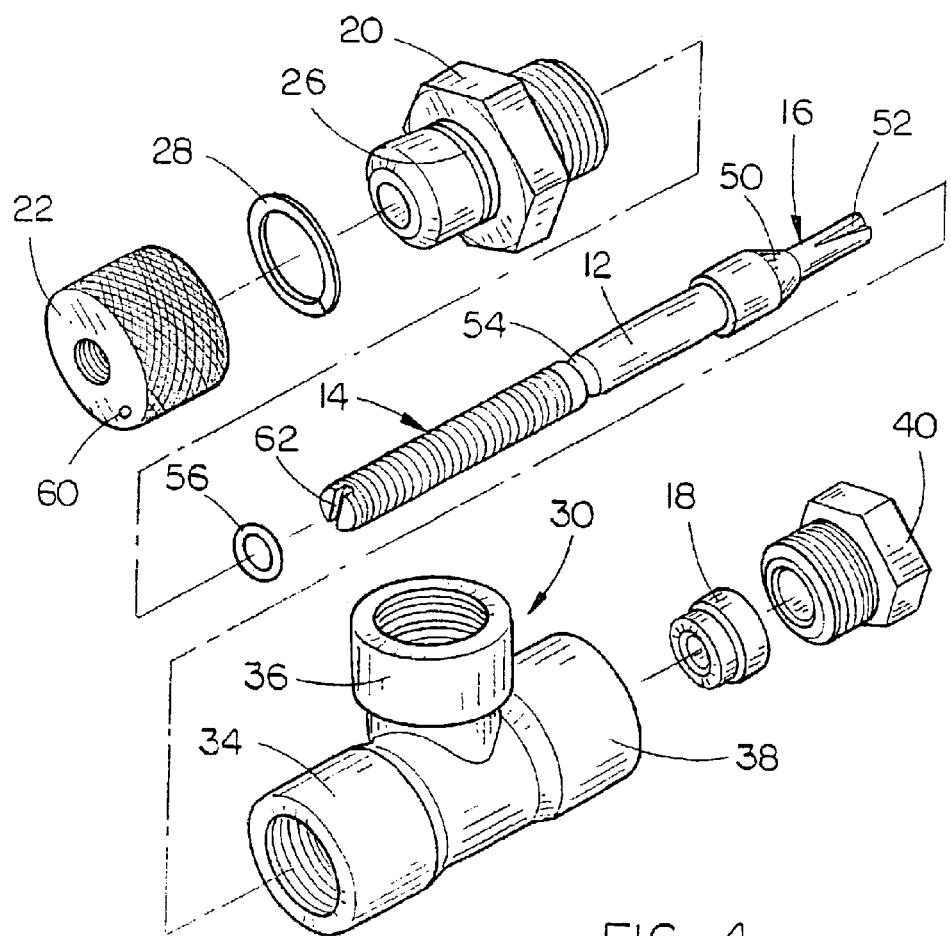
FIG. 4 is a perspective exploded view of the component parts of at least one embodiment of the metering valve of the present invention.
Figure 5:
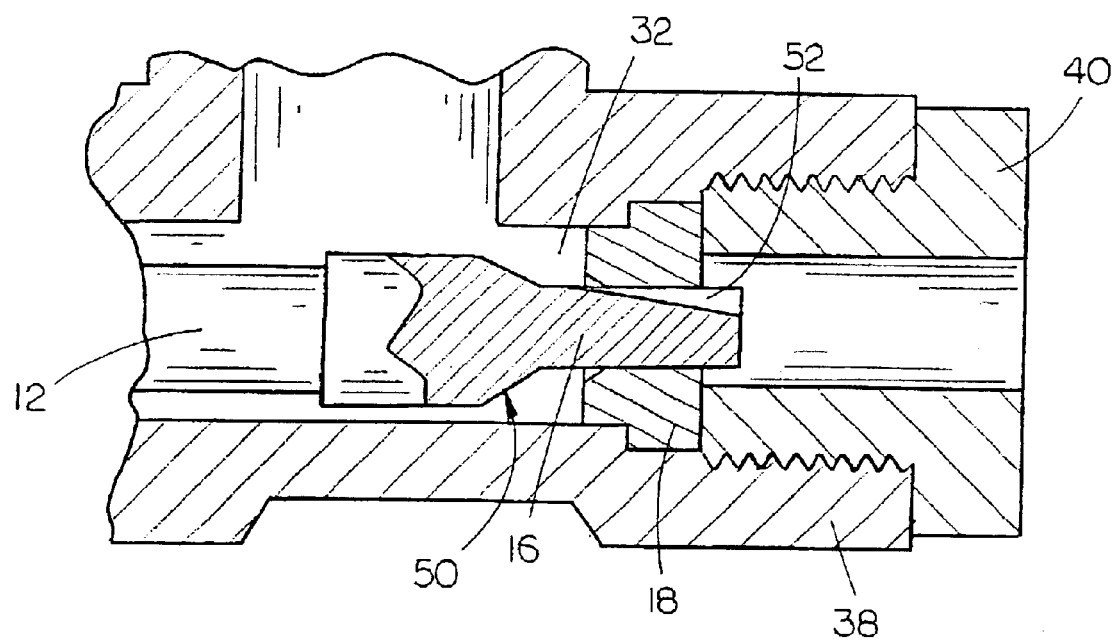
FIG. 5 depicts a partial cutaway view of the valve stem and valve seat of one embodiment of the present invention.

A valve housing 30 is provided to encase the inner working members of the valve assembly 10 and provide a fluid passageway 32. It is contemplated that the housing 30 could be formed in nearly any configuration as the circumstances so require; however, in a preferred embodiment, the housing 30 is provided in the shape of a tee connector. The housing 30, as depicted in FIGS. 2–4, is provided with an adjustment end 34, a fluid input end 36, and a fluid output end 38. The adjustment end 34 is open and preferably provided with mating threads, or other known mating structures, to receive the lower threaded end of the adjustment coupling member 20. The fluid input end 36 is open and preferably provided with any known mating structure, such as mating threads, to operatively connect the valve assembly 10 to a fluid source. The fluid output end 38 is also open and preferably provided with a mating structure, such as mating threads, to releasably engage an output coupling member 40, which is operatively connected to one or more known fluid dispersal devices. With the output coupling member 40 coupled to the fluid output end 38, the valve seat 18 is firmly secured in an operational position within the valve housing 30, as depicted in FIG. 3.

In use, fluid is provided from a fluid supply, such as the applicator 42 depicted in FIG. 1. The fluid applicator 42, which is provided with a holding tank 44, a strainer 46, and pump member 48, is a typical example of an agricultural use for the valve assembly 10. However, it is contemplated that the valve assembly 10 will, with little, if any, modification, be appropriate for use in most gas and liquid applications, such as medical and biochemical gas applications, research laboratory sampling, and other such uses in a varying array of fields. In the example depicted, the pump member 48 draws the liquid chemical from the applicator 42 and delivers it to the fluid input end 36 of the valve housing 30, introducing the fluid to the fluid passageway 32.

Figure 6:
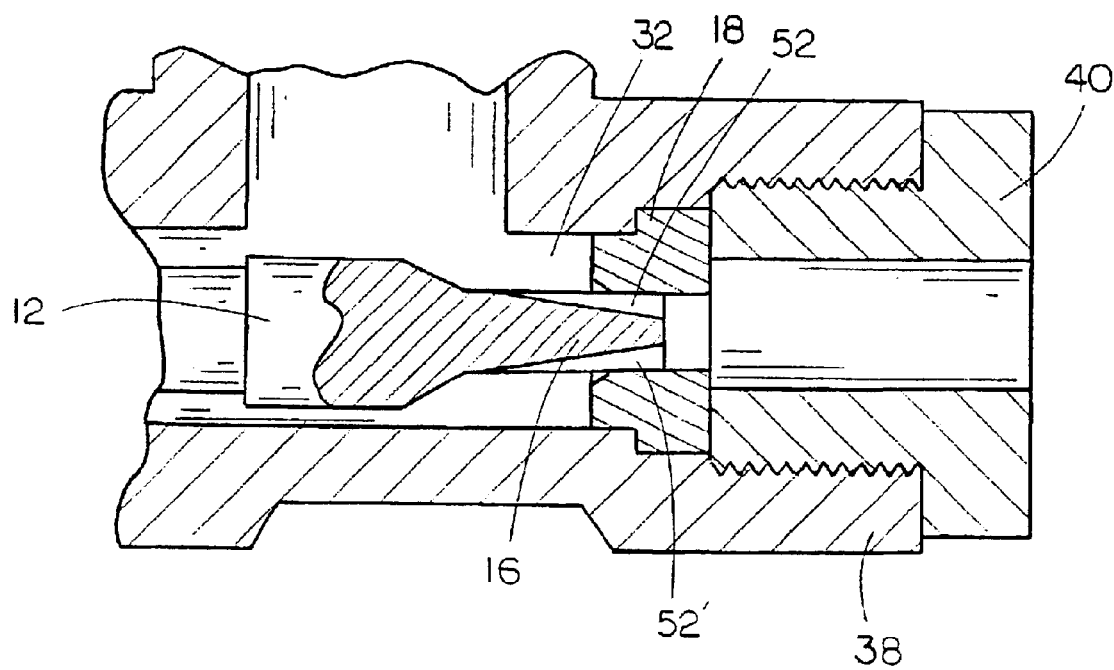
FIG. 6 is a partial cutaway view of another possible embodiment of the valve stem and valve seat of the present invention.

By rotating the adjustment knob 22 in a counterclockwise direction, the user incrementally advances the valve stem 10 in a linear direction toward the valve seat 18. Continued rotation of the adjustment knob 22 will dispose the regulating end 16 of the valve stem 12 within the opening of the valve seat 18 until the tapered shoulder portion 50 of the valve stem 12 is engaged with the valve seat 18. In this position, fluid is prohibited from passing through the valve seat 18 from the fluid passageway 32. As the user rotates the adjustment knob 22 in a clockwise direction, the regulating end 16 of the valve stem 12 is incrementally withdrawn from within the opening of the valve seat 18. An elongated groove 52, which is formed within the regulating end 16 of the valve stem 12, provides the pathway in which the fluid is permitted to travel from the fluid passageway 32 to the open interior of the output coupling member 40. Preferably, the elongated channel 52 is tapered in shape and extends longitudinally along the valve stem 12 so that the aperture through which the fluid passes from fluid passageway 32 into the open inner chamber of output coupling member 40 gradually increases as the user withdraws the regulating end 16 of the valve stem 12 from within the valve seat 18. The rate of groove taper per unit length is preselected to provide the desired ratio of rotation of adjustment knob 22 to fluid flow. It is preferred that the regulating end 16 of the valve stem 12 be capable of complete withdrawal from within the valve seat 18 to allow for the purging of any obstructions or debris from the valve seat 18 and the fluid passageway 32.

Where a large volume of fluid flow is required, the regulating end 16 of the valve stem 12 can be provided with a plurality of elongated channels 52. FIG. 6 depicts one such embodiment where the regulating end 16 is provided with a first elongated channel 52 and a second elongated channel 52'. Moreover, it is contemplated that the shapes of the channel members 52 and 52' can be provided in any length, width and depth permitted by the size of the regulating end 16 of the valve stem 12 in order to vary the manner in which the fluid flow is regulated. It is further contemplated that the shape of the channel members 52 and 52' can be provided in a gradual taper, a stepped fashion, or any other such shape as desired to provide a variable and wide range of incremental flow rates.

To prevent the passage of the fluid out of the valve assembly 10 from between the valve stem 12 and the adjustment coupling member 20, a generally annular recess 54 is formed in the valve stem 12 as shown in FIG. 3. The annular recess 54 is shaped to receive an O-ring 56 or similar known sealing device. It is preferred that the annular recess 54 and the O-ring 56 be positioned so that they are disposed within the opening of the adjustment coupling member 20 when the valve assembly 10 is in use. Engagement of the O-ring 56 with the inner walls of the adjustment coupling member 20 and the annular recess 54 substantially prevents fluid passage and further assists in preventing rotation of the valve stem 12 when the adjustment knob 22 is rotated. However, it is contemplated that the O-ring 56 would provide insufficient frictional engagement with the inner walls of the adjustment coupling member 20 to prevent the unintended withdrawal of the valve stem 12 from the valve assembly 10 through the occurrence of a dramatic increase in fluid pressure or other similar event. Accordingly, it is preferred that a hip member 58 be formed in the valve stem 12. The hip member 58 should be provided with a shape and/or diameter that is incapable of passing through the opening of the adjustment coupling member 20. In this manner, a positive stop is provided to prevent the unintended withdrawal of the valve stem 12.

Adjustment knob 22 is preferably provided with an indicator 60 to provide the user a point of reference regarding the number of rotations performed. A calculation of the corresponding relationship between the size of the elongated channel member 52, the sizes and geometry of the adjustment knob 22 and the adjustment end 14 of the valve stem 12, along with the pressure at which the fluid is supplied to the valve assembly 10, will provide a correlation between the number of turns of the knob 22 and the volume of fluid flow through the valve system 10. A groove 62, formed in the end 14 of the valve stem 12, provides an aligning reference to use in conjunction with the indicator 60.

It is preferred that the groove 62 be formed in a shape that can be received by a screwdriver or other such tool so that the valve stem 12 can be rotated with respect to the adjustment knob 22 and the adjustment coupling member 20. This provides a second manner in which the valve stem 12 can be moved reciprocally with respect to the remaining structural components of the valve assembly 10. Accordingly, the user will be able to make minute adjustments of the location of the valve stem 12 with respect to the valve seat 18 and/or the adjustment knob 22 with relative ease, regardless of operating conditions or location. Moreover, the channel 62 provides a manner in which the user can clean and repair the valve assembly 10 if the adjustment knob 22 and the valve stem 12 have become fouled with dirt or other debris and are no longer rotatable with respect to one another.

The limited number of functional parts to the valve assembly 10 provides ease of manufacture as well as assembly and use. The valve assembly 10 is easily disassembled to allow for cleaning and maintenance as well as the exchange of different component parts, such as a valve stem having a tapered regulating end portion 16 or a valve stem with multiple channel members 52 and 52', for a valve stem 12 having only one channel member 52. Accordingly, it is further contemplated that the respective diameters of the opening in valve seat 18 and the regulating end portion 16 of the valve stem could be fabricated to be larger or smaller to further provide an additional interchangeable variable flow system.

In the drawings and in the specification, there have been set forth preferred embodiments of the invention; and although specific items are employed, these are used in a generic and descriptive sense only and not for purposes of limitation. Changes in the form and proportion of parts, as well as substitute of equivalents, are contemplated as circumstances may suggest or render expedient without departing from the spirit or scope of the invention as further defined in the following claims.

Thus it can be seen that the invention accomplishes at least all of its stated objectives.

I claim:

1. A valve assembly, comprising:
 a valve housing having an input portion, an output portion, an adjustment portion and
 an inner chamber; said input portion being in open fluid communication with said output portion;
 an elongated valve stem having an adjustment end portion and a flow regulating end portion; said valve stem being at least partially disposed within the inner chamber of said valve housing so that said valve stem extends generally coaxially with the adjustment and output portions of said valve housing;
 first adjustment means operatively coupled to the adjustment portion of said valve housing for selective, reciprocal, substantially non-rotational movement of said valve stem with respect to said valve housing;
 second adjustment means operatively coupled to the adjustment portion of said valve housing for selective, reciprocal, rotational movement of said valve stem with respect to said valve housing; and
 a valve seat having an opening formed coaxially therethrough; said valve seat being positioned at least partially within the inner chamber of said valve housing adjacent said output end portion;
 said flow regulation end portion of said valve stem being sized to be selectively slidably received within the opening of said valve seat.

2. The valve assembly of claim 1 wherein the flow regulation end portion of said valve stem has at least one flow channel formed therein; said at least one flow channel being selectively positionable with respect to the opening in said valve seat to regulate the fluid communication between the input and output portions of said valve housing.

3. The valve assembly of claim 2 wherein said at least one flow channel is shaped to permit graduated regulation of the fluid communication between the input and output portions of said valve housing.

4. The valve assembly of claim 3 wherein said at least one flow channel is tapered.

5. The valve assembly of claim 1 wherein the flow regulation end portion of said valve stem is provided with a plurality of flow channels formed therein; said plurality of flow channels being selectively positionable with respect to the opening in said valve seat to regulate the fluid communication between the input and output end portions of said valve housing.

6. The valve assembly of claim 1 wherein the flow regulation end portion of said valve stem is generally tapered in shape; said flow regulation end portion of said valve stem being selectively positionable with respect to the opening in said valve seat to regulate the fluid communication between the input and output end portions of said valve housing.

7. The valve assembly of claim 1 wherein said valve stem is provided with a shoulder portion intermediate the adjustment end and flow regulating end portions of said valve stem; said shoulder portion being selectively engageable with the opening in said valve seat to substantially terminate the open fluid communication between the input and output portions of said valve housing.

8. The valve assembly of claim 1 further comprising an adjustment coupling member having first and second end portions and an opening formed between said first and second end portions: said first end portion of said adjustment coupling member being operatively coupled to said adjustment knob; said second end portion of said adjustment coupling being operatively coupled to the adjustment portion of said valve housing; said opening of said adjustment coupling member being shaped to selectively slidably receive the adjustment end portion of said valve stem therethrough.

9. The valve assembly of claim 8 wherein said valve stem is further provided with a hip member intermediate the adjustment end and regulating end portions of said valve stem; said hip member having a shape that resists the passing of said hip member through the opening in said adjustment coupling member.

10. The valve assembly of claim 1 further comprising an applicator coupling operatively coupled to the output end of said valve housing; said applicator coupling having an opening formed therethrough which is in open fluid communication with the opening in said valve seat.

11. The valve assembly of claim 1 wherein said second adjustment means is comprised of a channel member transversely disposed in the adjustment end portion of said valve stem.

12. The valve assembly of claim 1 wherein said first adjustment means is comprised of an adjustment knob operatively rotatably coupled to the adjustment end of said valve stem.

13. The valve assembly of claim 12 wherein said adjustment knob is provided with an indicator means for determining a degree of rotation undertaken by said adjustment knob with respect to said valve stem.

14. The valve assembly of claim 2 further comprising an alternate elongated valve stem having an adjustment end portion, a flow regulation end portion, and a plurality of elongated channels formed in said flow regulation end portion; said alternate valve stem being selectively exchangeable with said valve stem within the valve assembly to provide an alternate manner for regulating the fluid communication between the input and output portions of said valve housing.

15. The valve assembly of claim 2 further comprising an alternate elongated valve stem having an adjustment end portion, a flow regulation end portion, and a tapered regulation end portion; said alternate valve stem being selectively exchangeable with said valve stem within the valve assembly to provide an alternate manner for regulating the fluid communication between the input and output portions of said valve housing.

16. A valve assembly, comprising:

a housing having at least an input end, an output end and an open inner chamber extending between said input and output ends;

a valve seat having an opening formed therethrough; said valve seat being positioned generally intermediate the input and output ends of said housing;

stem means reciprocally movable within said housing for selective engagement with said valve seat for incremental regulation of a flow of fluid between the input and output ends of said housing;

adjustment means, operatively connected to said stem means and said housing, for reciprocal movement of said stem means with respect to said valve seat and further comprising a second adjustment means operatively connected to said housing and said stem means, for reciprocal movement of said stem means with respect to said valve seat.

17. The valve assembly of claim 16 wherein said second adjustment means provides rotational and reciprocal movement of said stem means with respect to said valve seat.

18. The valve assembly of claim 16 further comprising a second stem means for selective exchange with said stem means to provide the valve assembly with an alternate manner of incremental regulation of said flow of fluid between the input and output ends of said housing.

* * * * *